US012709636B2

(12) United States Patent
Garces et al.

(10) Patent No.: US 12,709,636 B2
(45) Date of Patent: Aug. 18, 2026

(54) IMMUNOGENS DERIVED FROM SARS-CoV2 SPIKE PROTEIN

(71) Applicant: AMGEN INC., Thousand Oaks, CA (US)

(72) Inventors: Fernando Garces, San Francisco, CA (US); Zhulun Wang, Los Altos, CA (US); Timothy Riley, Moorpark, CA (US)

(73) Assignee: AMGEN INC., Thousand Oaks, CA (US)

(*) Notice: Subject to any disclaimer, the term of this patent is extended or adjusted under 35 U.S.C. 154(b) by 670 days.

(21) Appl. No.: 18/006,689

(22) PCT Filed: Jul. 22, 2021

(86) PCT No.: PCT/US2021/042836
§ 371 (c)(1),
(2) Date: Jan. 24, 2023

(87) PCT Pub. No.: WO2022/020636
PCT Pub. Date: Jan. 27, 2022

(65) Prior Publication Data

US 2023/0322867 A1 Oct. 12, 2023

Related U.S. Application Data

(60) Provisional application No. 63/056,396, filed on Jul. 24, 2020.

(51) Int. Cl.
*C07K 14/165* (2006.01)
*C07K 16/10* (2026.01)
*C12N 15/85* (2006.01)
*A61K 39/00* (2006.01)

(52) U.S. Cl.
CPC ............ *C07K 14/165* (2013.01); *C07K 16/10* (2013.01); *C12N 15/85* (2013.01); *A61K 2039/505* (2013.01); *C12N 2770/20034* (2013.01)

(58) Field of Classification Search
None
See application file for complete search history.

(56) References Cited

U.S. PATENT DOCUMENTS 4,399,216 A 8/1983 Axel et al.
4,510,245 A 4/1985 Cousens et al.
4,634,665 A 1/1987 Axel et al.
4,740,461 A 4/1988 Kaufman
4,912,040 A 3/1990 Kaufman et al.
4,959,455 A 9/1990 Clark et al.
4,968,615 A 11/1990 Koszinowski et al.
5,151,510 A 9/1992 Stec et al.
5,168,062 A 12/1992 Stinski
5,179,017 A 1/1993 Axel et al.
5,545,806 A 8/1996 Lonberg et al.
5,545,807 A 8/1996 Surani et al.
5,569,825 A 10/1996 Lonberg et al.
5,591,669 A 1/1997 Krimpenfort et al.
5,612,205 A 3/1997 Kay et al.
5,625,126 A 4/1997 Lonberg et al.
5,633,425 A 5/1997 Lonberg et al.
5,643,763 A 7/1997 Dunn et al.
5,661,016 A 8/1997 Lonberg et al.
5,721,367 A 2/1998 Kay et al.
5,770,429 A 6/1998 Lonberg et al.
5,789,215 A 8/1998 Berns et al.
5,789,650 A 8/1998 Lonberg et al.
5,814,318 A 9/1998 Lonberg et al.
5,916,771 A 6/1999 Hori et al.
5,939,598 A 8/1999 Kucherlapati et al.
5,985,615 A 11/1999 Jakobovits et al.
5,994,619 A 11/1999 Stice et al.
5,998,209 A 12/1999 Jokobovits et al.
6,075,181 A 6/2000 Kucherlapati et al.
6,091,001 A 7/2000 Jakobovits et al.
6,114,598 A 9/2000 Kucherlapati et al.
6,130,364 A 10/2000 Jakobovits et al.
6,150,584 A 11/2000 Kucherlapati et al.
6,162,963 A 12/2000 Kucherlapati et al.
6,517,529 B1 2/2003 Quinn

FOREIGN PATENT DOCUMENTS

EP 0338841 A1 10/1989
EP 0216846 B1 1/1990
EP 0256055 B1 8/1991

(Continued)

OTHER PUBLICATIONS

Altschul, S.F., et al., "Gapped BLAST and PSI-BLAST: A New Generation of Protein Database Search Programs," Nucleic Acids Research 25(17):3389-3402, Oxford University Press, England (1997).
Altschul, SF et al., "Basic Local Alignment Search Tool," J Mol Biol, 1990, vol. 215, pp. 403-410, 8 pages.
Ausubel et al, Current Protocols in Molecular Biology, Greene Publishing Associates (1992).

(Continued)

*Primary Examiner* — Nicole Kinsey White
(74) *Attorney, Agent, or Firm* — Jonathan M. Dermott

(57) ABSTRACT

The present invention relates to severe acute respiratory syndrome coronavirus 2 ("SARS-CoV2") immunogens useful for the generation of therapeutic antibodies and vaccine development. Such therapeutic antibodies include human antibodies and antigen-binding portions thereof that specifically bind to human SARS-CoV2 S protein, and that function to neutralize SARS-CoV2. The present invention also relates to methods of generating antibodies and antigen-binding portions thereof that specifically bind to human SARS-CoV2 S protein.

7 Claims, 11 Drawing Sheets

Specification includes a Sequence Listing.

(56) References Cited

FOREIGN PATENT DOCUMENTS

| | | | | | |
|---|---|---|---|---|---|
| EP | 0323997 | B1 | | 4/1993 | |
| WO | 91/10741 | A1 | | 7/1991 | |
| WO | 94/02602 | A1 | | 2/1994 | |
| WO | 96/33735 | A1 | | 10/1996 | |
| WO | 96/34096 | A1 | | 10/1996 | |
| WO | 98/16654 | A1 | | 4/1998 | |
| WO | 98/24893 | A3 | | 8/1998 | |
| WO | 98/50433 | A2 | | 11/1998 | |
| WO | 99/45031 | A2 | | 9/1999 | |
| WO | 99/53049 | A1 | | 10/1999 | |
| WO | 00/09560 | A2 | | 2/2000 | |
| WO | 00/37504 | A2 | | 6/2000 | |
| WO | WO-2021211688 | A1 | * | 10/2021 | ........... C07K 14/165 |

OTHER PUBLICATIONS

Babcook, J. S. et al., "A novel strategy for generating monoclonal antibodies from single, isolated lymphocytes producing antibodies of defined specificities" Proc. Natl. Acad. ScL, 1996, 93: 7843-7848.

Branden and Tooze, "Introduction to Protein Structure", Garland Publishing, Inc., New York, Table of Contents (1991).

Chothia et al., "Conformations of immunoglobulin hypervariable regions", Nature 342:878-883 (1989).

Chothia et al., "Canonical structures for the hypervariable regions of immunoglobulins," (1987) Journal of Molecular Biology 196(4):901-917.

Creighton (Ed.), Proteins, Structures and Molecular Principles, Freeman and Company, New York, TOC (1984).

Genbank Database [online], GenBank: QHS34546.1, Apr. 6, 2020, Internet, <URL: https://www.ncbi.nlm.nih.gov/protein/1804119761>, Aug. 4, 2025.

Gonnet GH., et al., "Exhaustive Matching of the Entire Protein Sequence Database" Science, vol. 256, Jun. 5, 1992, pp. 1443-1445.

Green et al., (1994) "Antigen-specific human monoclonal antibodies from mice engineered with human Ig heavy and light chain YACs", Nature Genetics 7:13-21.

Green LL., et al., "Regulation of B Cell Development by Variable Gene Complexity in Mice Reconstituted with Human Immunoglobulin Yeast Artificial Chromosomes", J. Exp. Med., vol. 188, 1998, pp. 483-495.

Harlow and Lane Antibodies: A Laboratory Manual, Cold Spring Harbor Laboratory Press, Cold Spring Harbor, N.Y. (1990).

Henderson et al., "Controlling the SARS-CoV-2 spike glycoprotein conformation" Nat. Struct. Mol. Biol, Nature Publishing Group, vol. 27, No. 10, Jul. 22, 2020, pp. 925-933.

Hsieh et al., "Structure-based Design of Prefusion-stabilized SARS-CoV-2 Spikes", bioRxiv, May 30, 2020, XP055806387.

International Preliminary Report on Patentability received for PCT Patent Application No. PCT/US21/42836, mailed on Feb. 2, 2023, 13 pages.

International Search Report and Written Opinion received for PCT Patent Application No. PCT/US21/42836, mailed on Jan. 24, 2022, 18 pages.

Invitation to Pay Additional Fees received for PCT Patent Application No. PCT/US21/42836, mailed on Nov. 30, 2021, 14 pages.

Kabat, Sequences of Proteins of Immunological Interest (National Institutes of Health, Bethesda, Md. (1987 and 1991)).

LaPlanche et al., Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric 0-ethyl phosphorothioates, Nucl. Acids Res., 14(22): 9081-93 (1986).

Mendez et al., Functional transplant of megabase human immunoglobulin loci recapitulates human antibody response in mice, Nat. Genet. 15:146-56 (1997).

Paul, W., ed., Fundamental Immunology, Chapter 7, 2d Edition, Raven Press, NY (1989).

Pearson WR., "Empirical Statistical Estimates for Sequence Similarity Searches", J Mol. Biol 276:71-84 (1998).

Pearson, "Effective protein sequence comparison", Methods Enzymol. 266:227-258 (1996).

Pearson, "Flexible sequence similarity searching with the FASTA3 program package", Methods Mol. Biol. 132:185-219 (2000).

Pearson, "Rapid and sensitive sequence comparison with FASTP and FASTA" Methods Enzymol. 183:63-98 (1990.

Pearson, "Using the FASTA program to search protein and DNA sequence databases" Methods Mol. Biol. 243:307-31 (1994).

Riley et al., "Enhancing the Prefusion Conformational Stability of SARS-CoV-2 Spike Protein Through Structure-Guided Design", Frontiers in Immunology, vol. 12, Apr. 22, 2021, XP055860865.

Saha P. et al., A virus that has gone viral: amino acid mutation in S protein of Indian isolate of Coronavirus COVID-19 might impact receptor binding, and thus, infectivity., May 29, 2020, BSR20201312, 40(5).

Sambrook et al., ed. (1989) Molecular Cloning a Laboratory Manual (2nd ed.; Cold Spring Harbor Laboratory Press).

Stec et al., Automated solid phase synthesis, separation and stereochemistry of phosphothioate analogues of oligodeoxyribonucleotides, J. Am. Chem. Soc., 106: 6077 (1984).

Stein et al., Physicochemical properties of phosphorothioate oligodeoxynucleotides, Nucl. Acids Res., 16(8): 3209-21 (1988).

Thornton et al., Prediction of Progress at Last, Nature (1991) 354:105-106.

Uhlmann and Peyman, "Antisense Oligonucleotides: A New Therapeutic Principle," Chemical Reviews, 1990, 90:543-584.

Ward, ES et al., "Binding activities of a repertoire of single immunoglobulin variable domains secreted from *Escherichia coli*," Nature, 1989, vol. 341, pp. 544-546, 3 pages.

Zon et al., Phosphorothioate oligonucleotides: Chemistry, purification, analysis, scale-up and future directions, Anti-Cancer Drug Design, 6(6): 539-68 (1991).

Zon et al.. Oligonucleotides and Analogues: A Practical Approach, pp. 87-108 (F. Eckstein, Ed., Oxford University Press, Oxford England (1991).

* cited by examiner

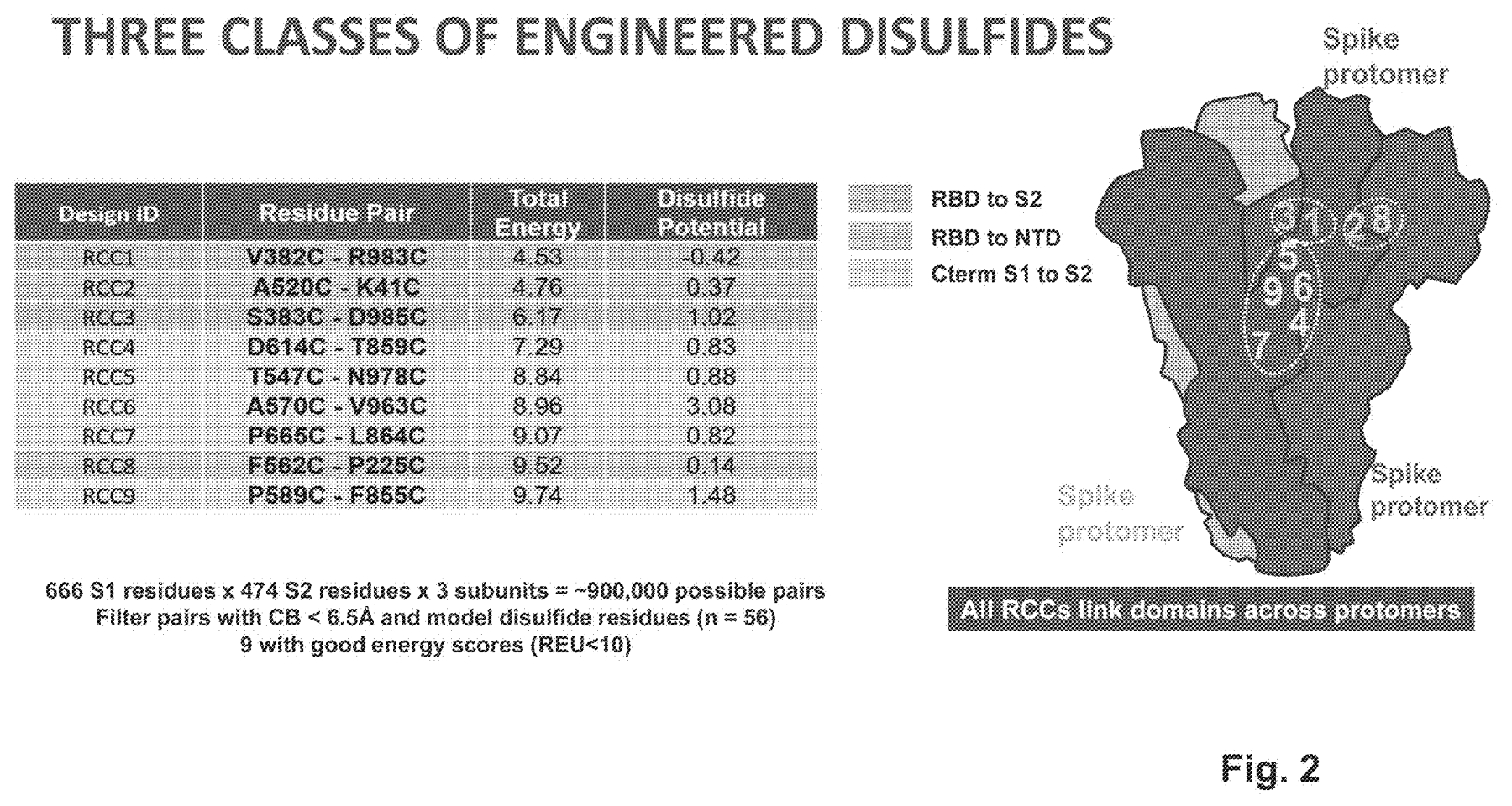

THREE CLASSES OF ENGINEERED DISULFIDES

| Design ID | Residue Pair | Total Energy | Disulfide Potential |
|---|---|---|---|
| RCC1 | V382C - R983C | 4.53 | -0.42 |
| RCC2 | A520C - K41C | 4.76 | 0.37 |
| RCC3 | S383C - D985C | 6.17 | 1.02 |
| RCC4 | D614C - T859C | 7.29 | 0.83 |
| RCC5 | T547C - N978C | 8.84 | 0.88 |
| RCC6 | A570C - V963C | 8.96 | 3.08 |
| RCC7 | P665C - L864C | 9.07 | 0.82 |
| RCC8 | F562C - P225C | 9.52 | 0.14 |
| RCC9 | P589C - F855C | 9.74 | 1.48 |

666 S1 residues x 474 S2 residues x 3 subunits ≈ ~900,000 possible pairs
Filter pairs with CB < 6.5Å and model disulfide residues (n = 56)
9 with good energy scores (REU<10)

Fig. 2

IMMUNOGENS DERIVED FROM SARS-CoV2 SPIKE PROTEIN

This application is a national stage application under 35 U.S.C. § 371 of International Application No. PCT/US2021/042836, having an international filing date of Jul. 22, 2021, which claims the benefit of U.S. Provisional Patent Application No. 63/056,396, filed on Jul. 24, 2020, which is hereby incorporated by reference in its entirety.

SEQUENCE LISTING

The present application is being filed along with a sequence listing in electronic format. The sequence listing is provided as a file entitled A-2657-US02-PCT Seglisting.txt; created on Jan. 23, 2023, which is 873 KB in size. The information in the electronic format of the sequence listing is incorporated herein by reference in its entirety.

BACKGROUND OF THE INVENTION

With the rise of COVID-19, the SARS CoV-2 spike(S) glycoprotein is a popular target for neutralizing antibodies and vaccine development. SARS-CoV2 mediates infection of target cells via the spike(S) protein expressed on the surface. The SARS CoV-2 Spike glycoprotein exists as a homotrimer, where each protomer consists of an N-terminal domain (NTD), Receptor Binding Domain (RBD), and S2 subunit. The NTD and RBD are part of the larger S1 subunit, which dissociates from the S2 subunit after binding ACE2 on the host cell. This induces global conformational change, leading to viral entry into the host cell. The three RBDs in the S protein trimer can exist in an "open" and "closed" configuration, but is sterically prevented from binding ACE2 in the "closed" conformation. Thus, the closed conformation is often described as the prefusion state and the open conformation is thought to be the initiation of the postfusion state, leading to S1 instability and dissociation.

The dynamic nature of the native S glycoprotein and structural transitions between pre- and postfusion states represent a challenge for prefusion targeting. With the dynamic nature of the S protein, there is a need and interest in stabilizing and further driving the S protein into the RBD-down, "prefusion" conformation. The present invention describes viable disulfides between the S1 and S2 subunits to produce several candidates to achieve the desired result of increased stability and conformational homogeneity.

SUMMARY OF THE INVENTION

In certain aspects, the disclosure provides an immunogen comprising a severe acute respiratory syndrome coronavirus 2 spike ("SARS-CoV2 S") polypeptide, wherein the polypeptide comprises one or more pairs of amino acid substitutions that correspond to residues selected from the group consisting of:

a) V382C and R983C of SEQ ID NO: 1;
b) A520C and K41C of SEQ ID NO: 1;
c) S383C and D985C of SEQ ID NO: 1;
d) D614C and T859C of SEQ ID NO: 1;
e) T547C and N978C of SEQ ID NO: 1;
f) A570C and V963C of SEQ ID NO: 1;
g) P665C and L864C of SEQ ID NO: 1;
h) F562C and P225C of SEQ ID NO: 1; and
i) P589C and F855C of SEQ ID NO: 1;

and wherein the polypeptide is 90%, 91%, 92%, 93%, 94%, 95%, 96%, 97%, and 98% identical to SEQ ID NO: 1.

In certain aspects, the disclosure provides an immunogen comprising a severe acute respiratory syndrome coronavirus 2 spike ("SARS-CoV2 S") polypeptide, wherein the polypeptide comprises one or more pairs of amino acid substitutions that correspond to residues selected from the group consisting of:

a) V382C and R983C of SEQ ID NO: 1;
b) A520C and K41C of SEQ ID NO: 1;
c) S383C and D985C of SEQ ID NO: 1;
d) D614C and T859C of SEQ ID NO: 1;
e) T547C and N978C of SEQ ID NO: 1;
f) A570C and V963C of SEQ ID NO: 1;
g) P665C and L864C of SEQ ID NO: 1;
h) F562C and P225C of SEQ ID NO: 1; and
i) P589C and F855C of SEQ ID NO: 1.

In certain embodiments, the polypeptide comprises amino acid substitutions that correspond to residues D614C, T859C, T547C and N978C.

In certain embodiments, the polypeptide further comprises one or more groups of amino acid substitutions that correspond to residues selected from the group consisting of:

a) K986P and V987P of SEQ ID NO: 1;
b) R682G, R683S, and R685S of SEQ ID NO: 1;
c) R682S, R683G, and R685G of SEQ ID NO: 1;
d) R682G, R683S, R685S, K986P and V987P of SEQ ID NO: 1; and
e) R682S, R683G, R685G, K986P and V987P of SEQ ID NO: 1.

In certain embodiments, the polypeptide has at least 97% sequence identity to SEQ ID NO: 1.

In certain embodiments, the polypeptide has at least 98% sequence identity to SEQ ID NO: 1.

In certain embodiments, the polypeptide has at least 99% sequence identity to SEQ ID NO: 1.

In certain embodiments, the polypeptide comprises an amino acid sequence selected from the group consisting of SEQ ID NOs: 13-21.

In certain embodiments, the polypeptide comprises an amino acid sequence selected from the group consisting of SEQ ID NOs: 4-12 and 44-61.

In certain embodiments, the polypeptide comprises a trimerization domain attached to the C-terminus of the immunogen.

In certain embodiments, the trimerization domain comprises the amino acid sequence of SEQ ID NO: 84 or SEQ ID NO: 85.

In certain embodiments, the polypeptide comprises an amino acid sequence selected from the group consisting of SEQ ID NOs: 23-40 and 63-80.

In certain aspects, the disclosure provides a method of producing antibodies that specifically bind SARS-CoV2 S polypeptide comprising administering to a non-human subject an immunogen of the present invention and a pharmaceutically acceptable delivery vehicle and/or adjuvant.

In certain aspects, the disclosure provides a method of treating COVID-19 in a subject comprising administering a therapeutically effective amount of an antibody produced by a method of the present invention and a pharmaceutically acceptable delivery vehicle to the subject.

In certain aspects, the disclosure provides a composition capable of producing an immunological response in a human subject, the composition comprising an immunogen of the present invention and a pharmaceutically acceptable delivery vehicle and/or adjuvant.

The invention contemplates combinations of any of the foregoing aspects and embodiments of the invention.

BRIEF DESCRIPTION OF THE DRAWINGS

FIG. 2 depicts various engineered disulfides and where they are located within the spike trimer.

DETAILED DESCRIPTION OF THE INVENTION

Figure 1:
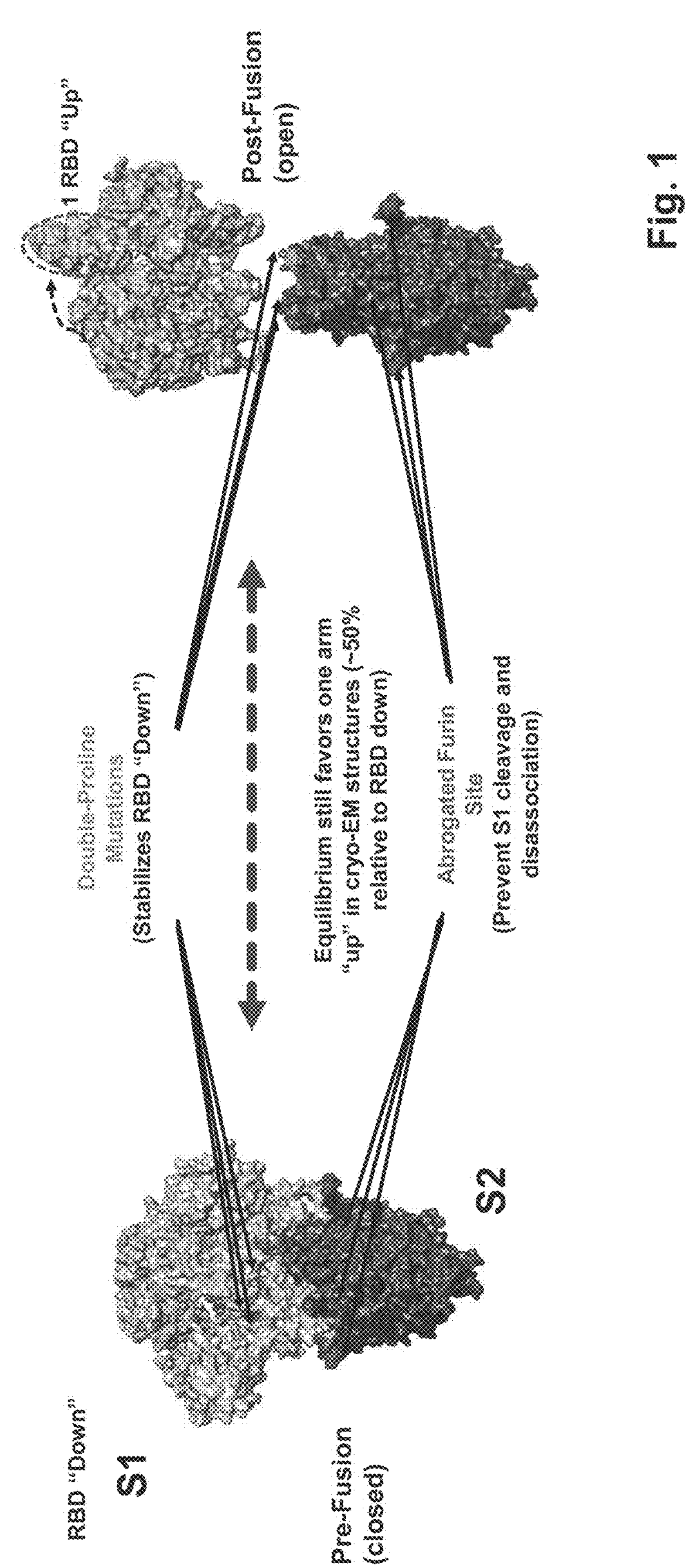
FIG. 1 depicts how the SARS-CoV-2 spike protein shows 2 main conformations: pre and post-fusion state.
Figure 3:
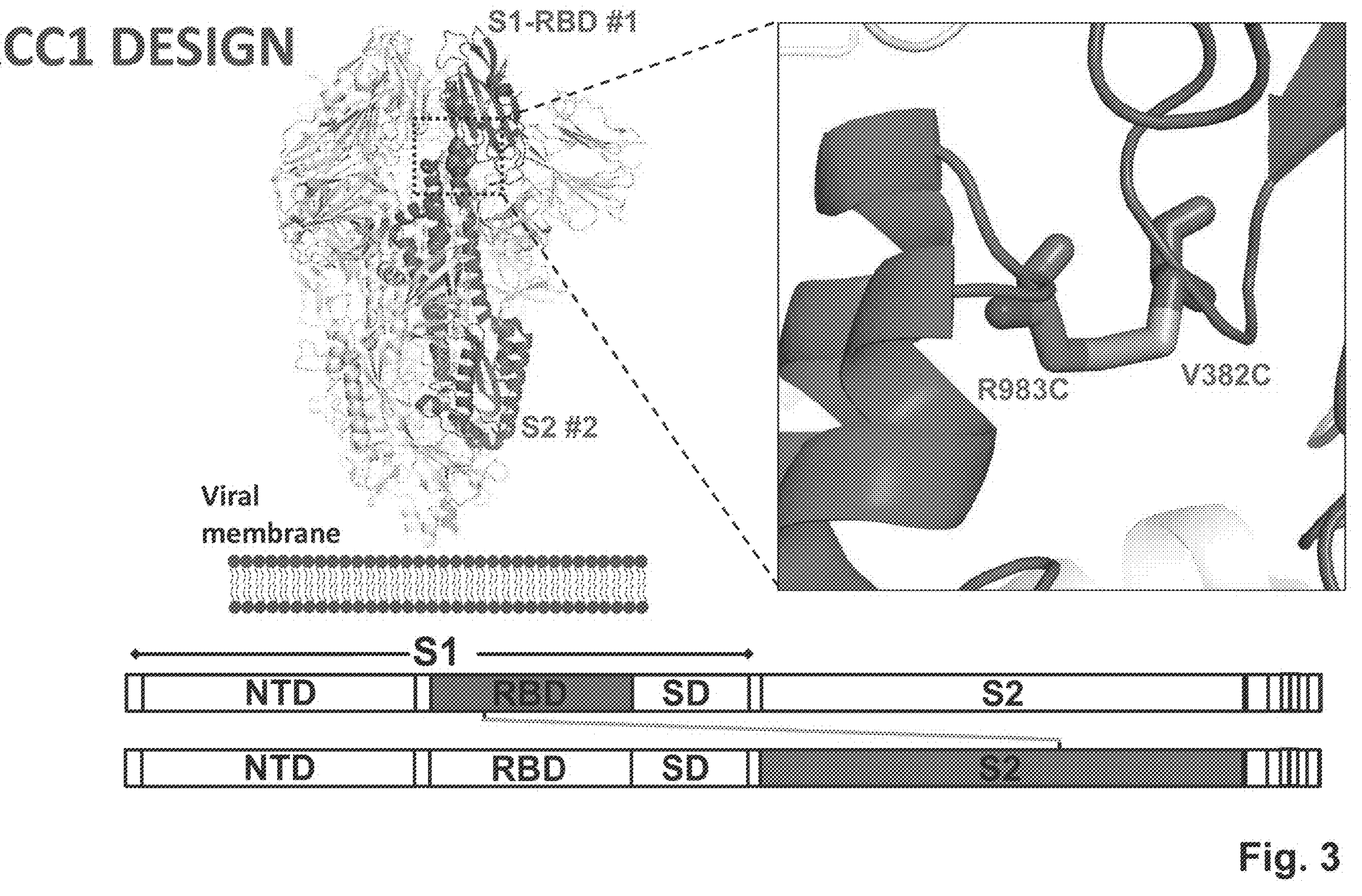
FIG. 3 depicts the positions and structural design of RCC1.
Figure 4:
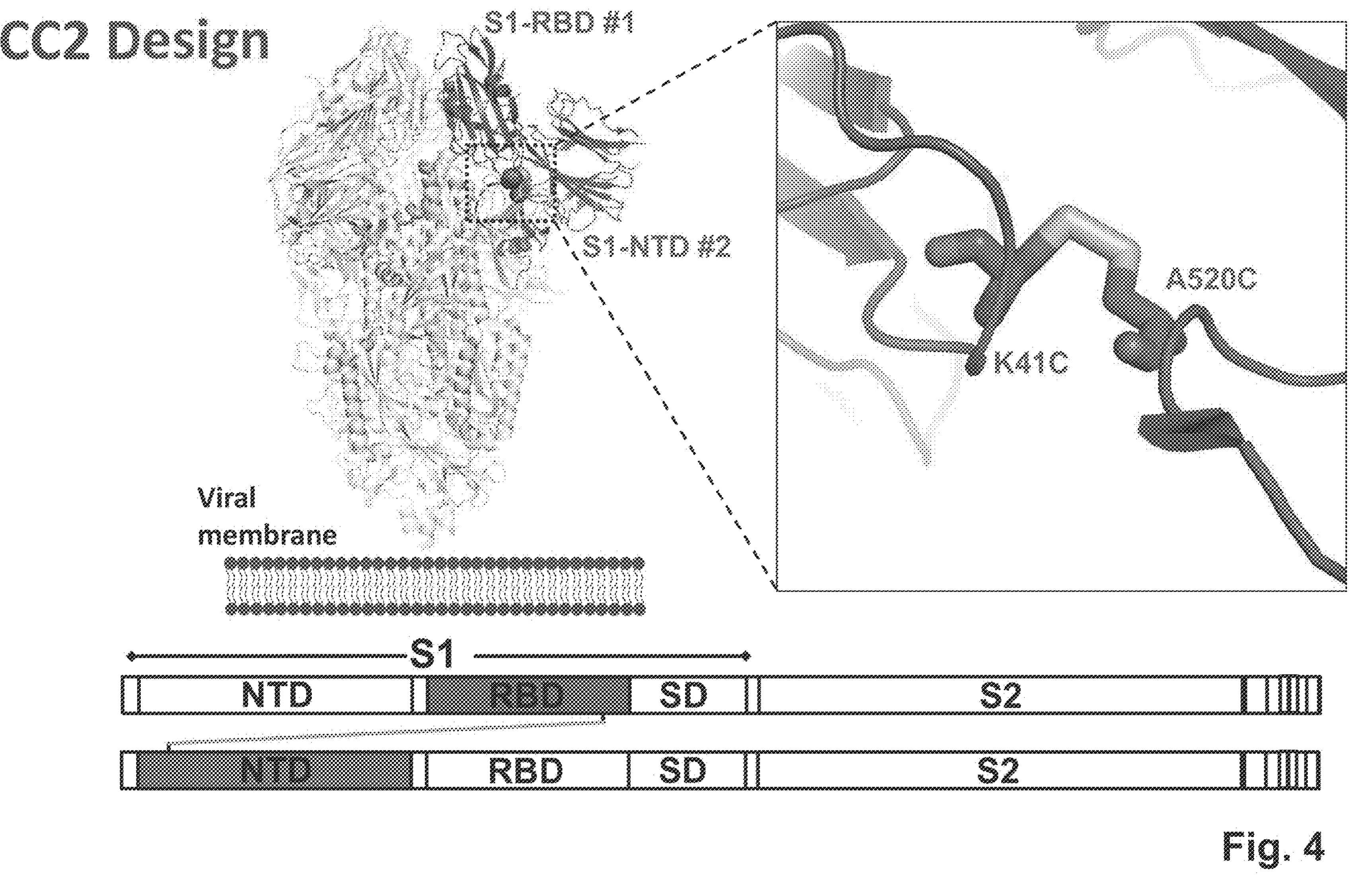
FIG. 4 depicts the positions and structural design of RCC2.
Figure 5:
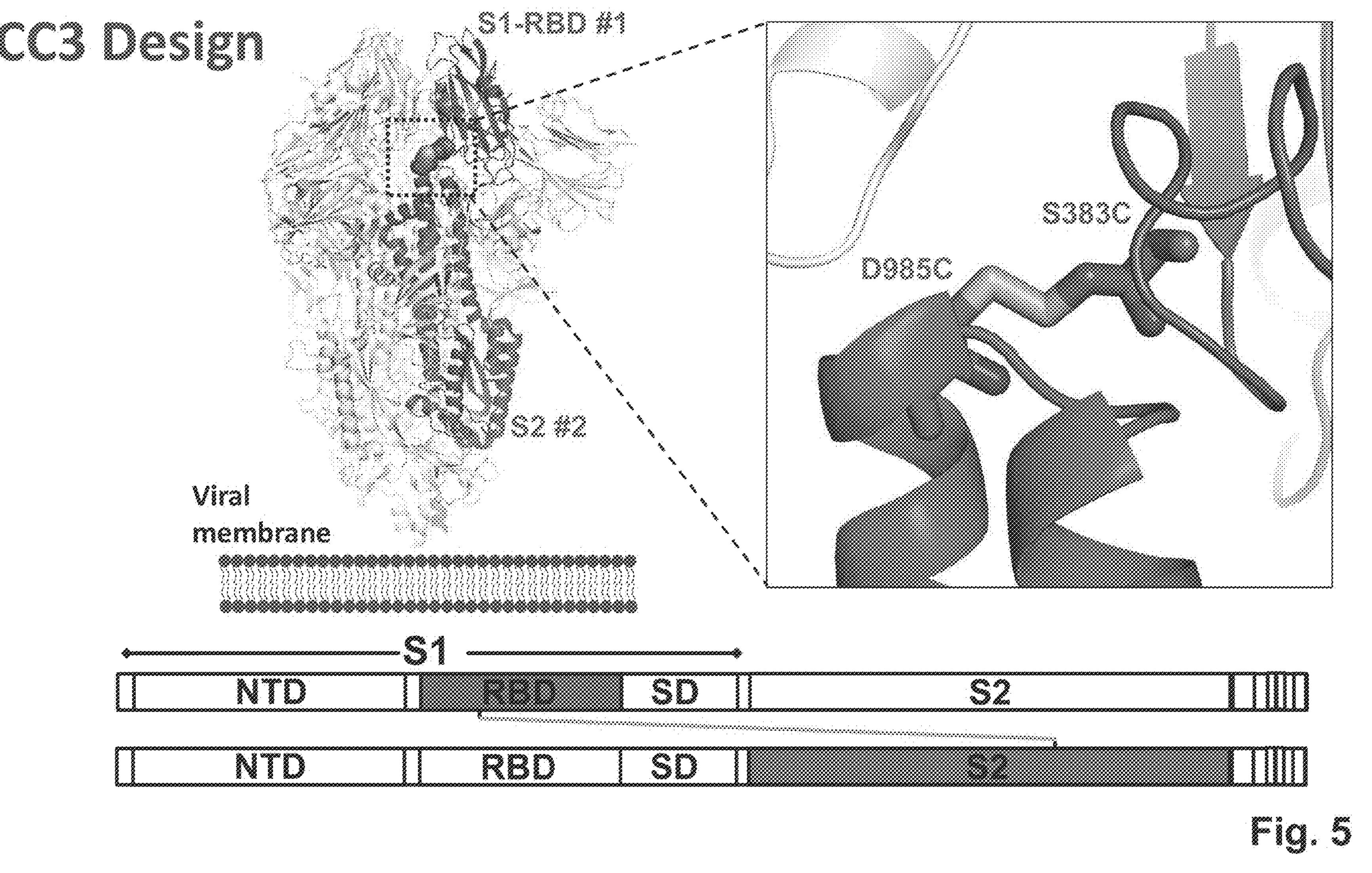
FIG. 5 depicts the positions and structural design of RCC3.
Figure 6:
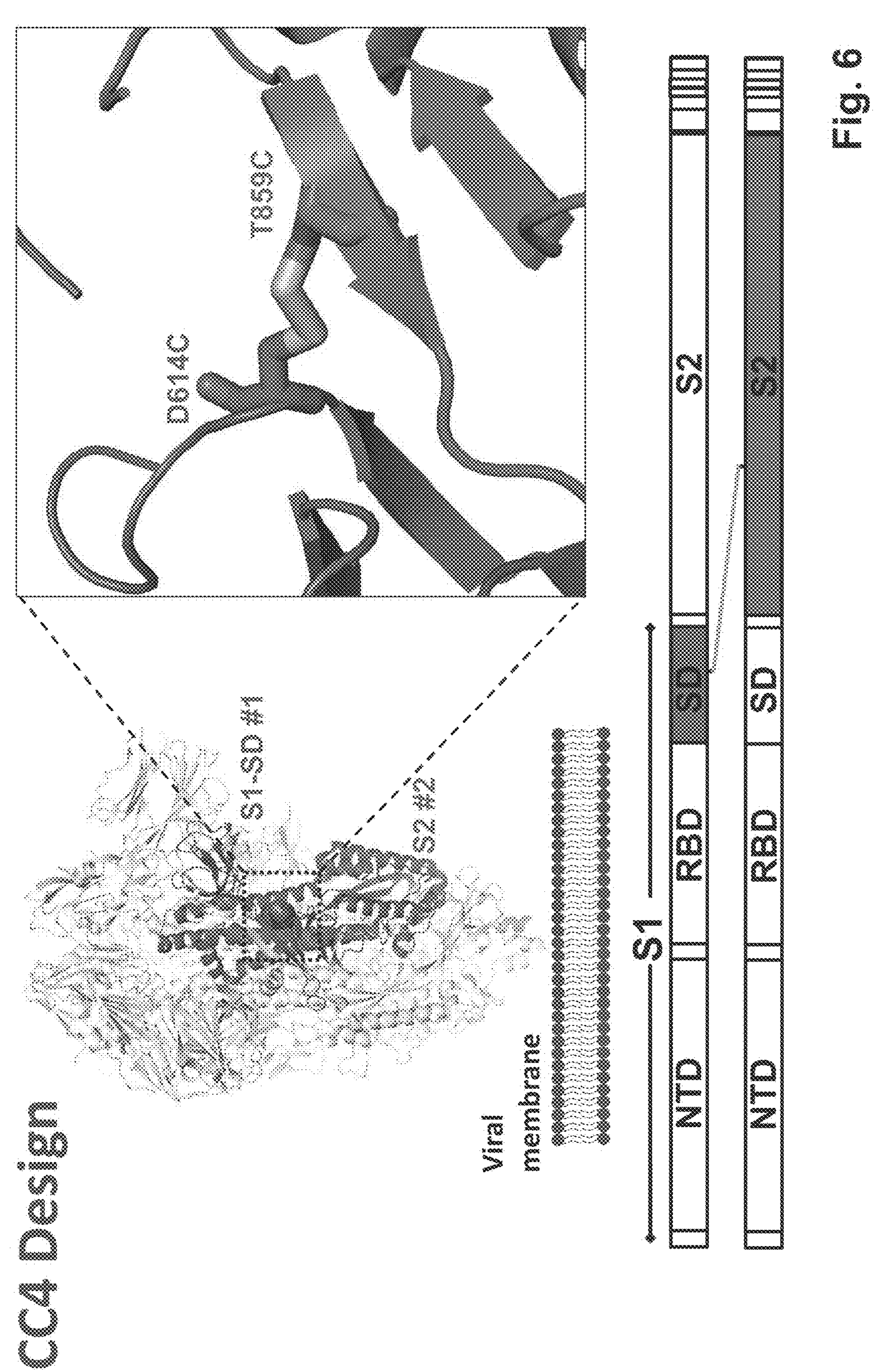
FIG. 6 depicts the positions and structural design of RCC4.
Figure 7:
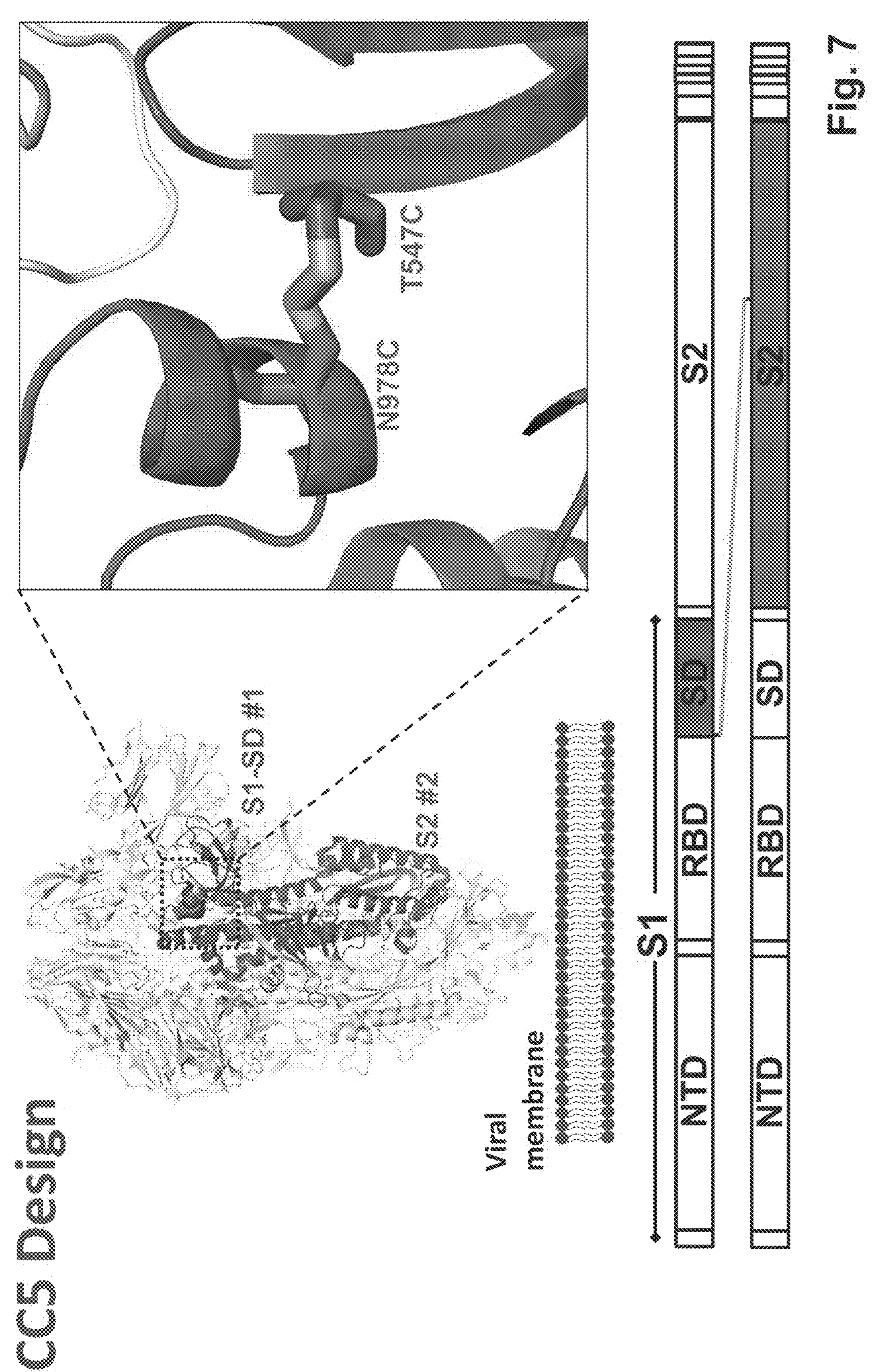
FIG. 7 depicts the positions and structural design of RCC5.
Figure 8:
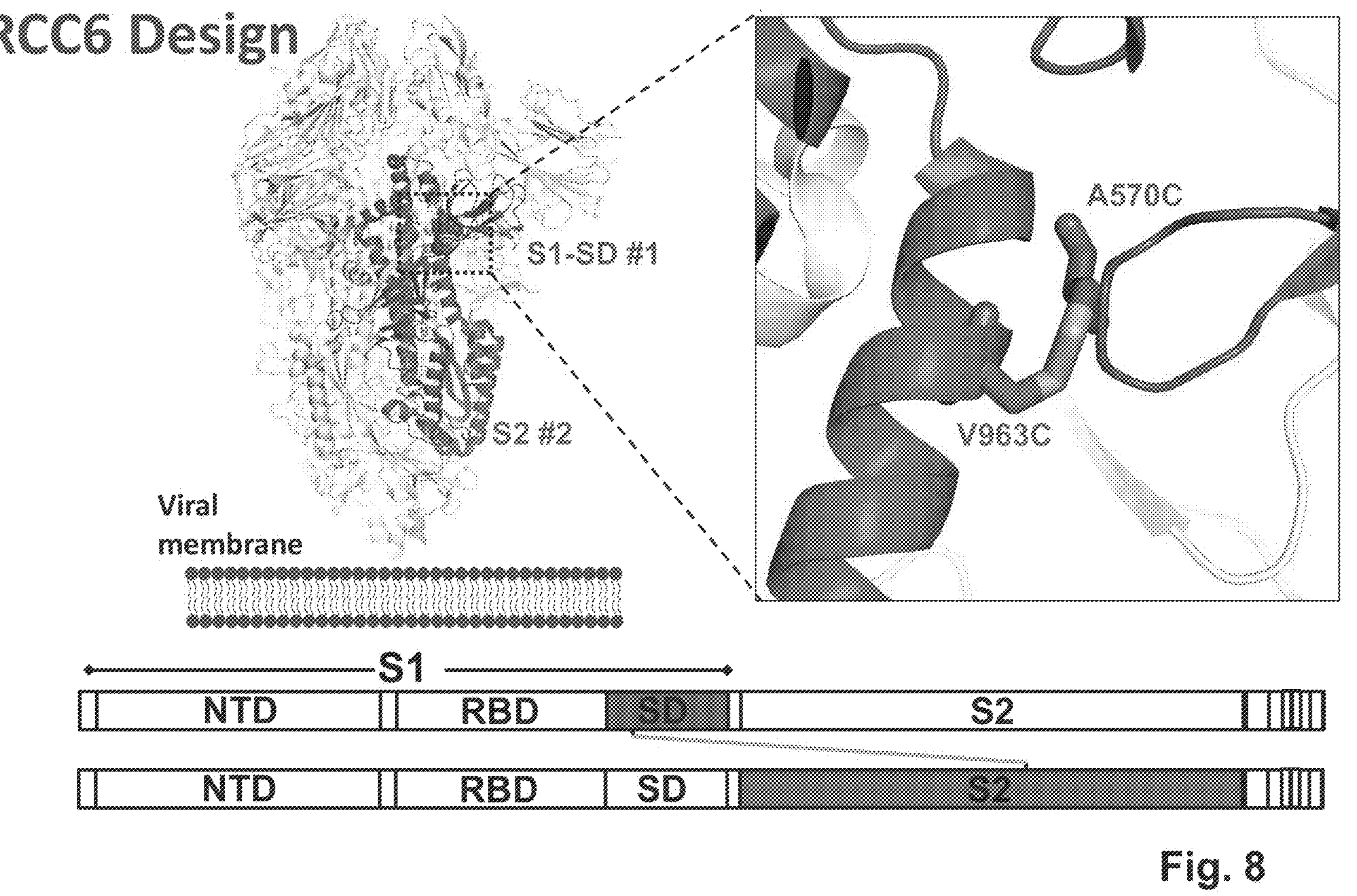
FIG. 8 depicts the positions and structural design of RCC6.
Figure 9:
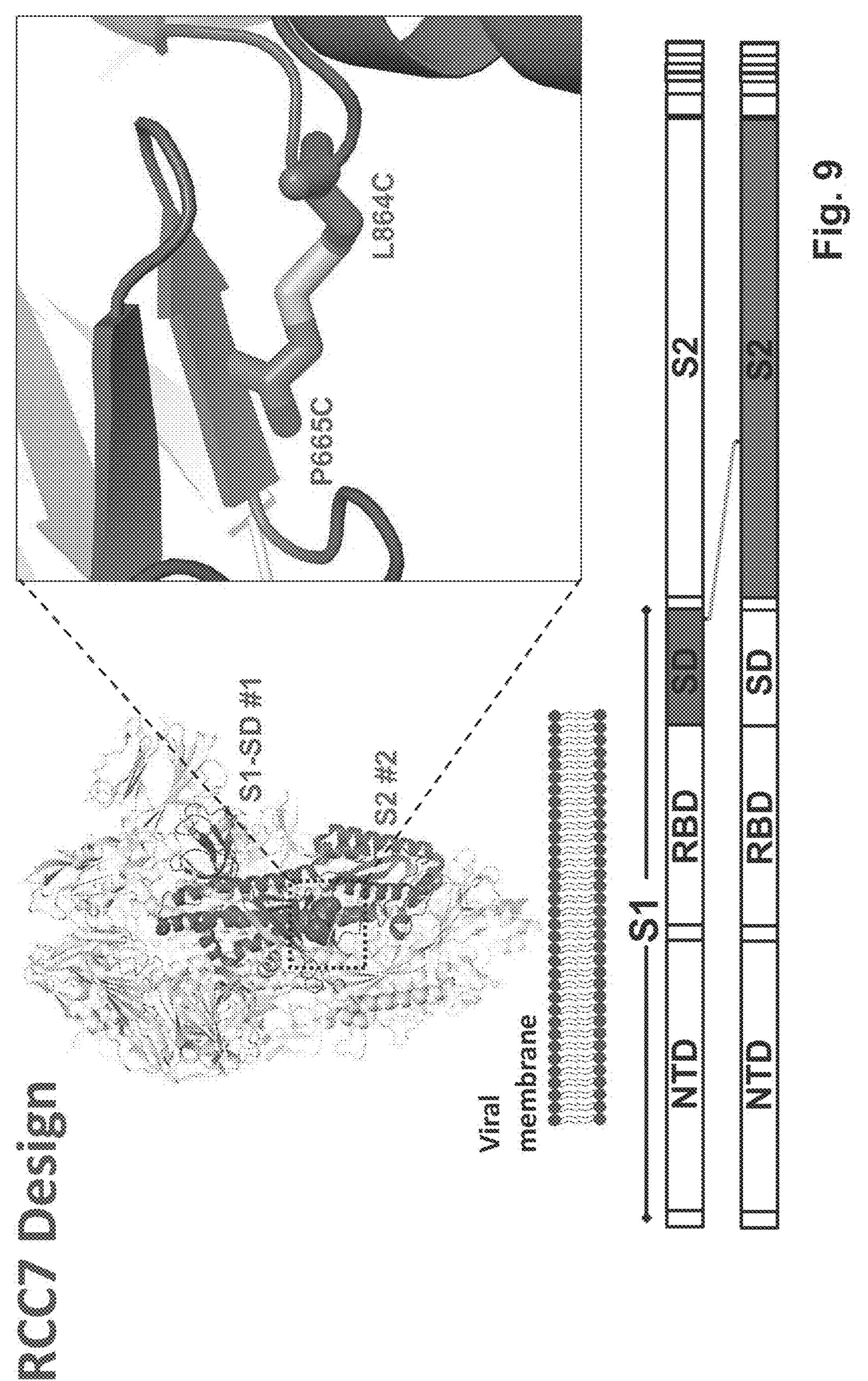
FIG. 9 depicts the positions and structural design of RCC7.
Figure 10:
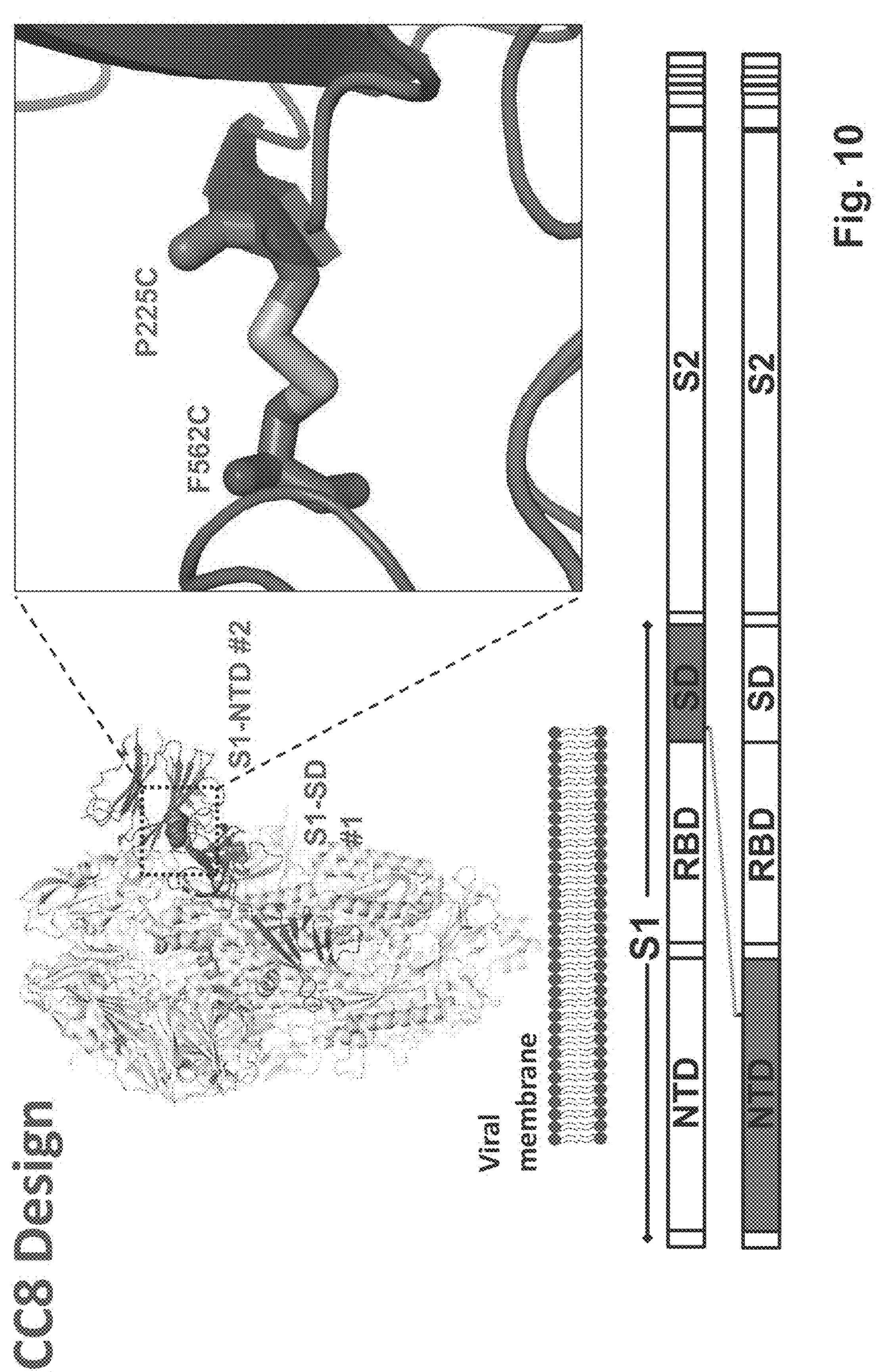
FIG. 10 depicts the positions and structural design of RCC8.
Figure 11:
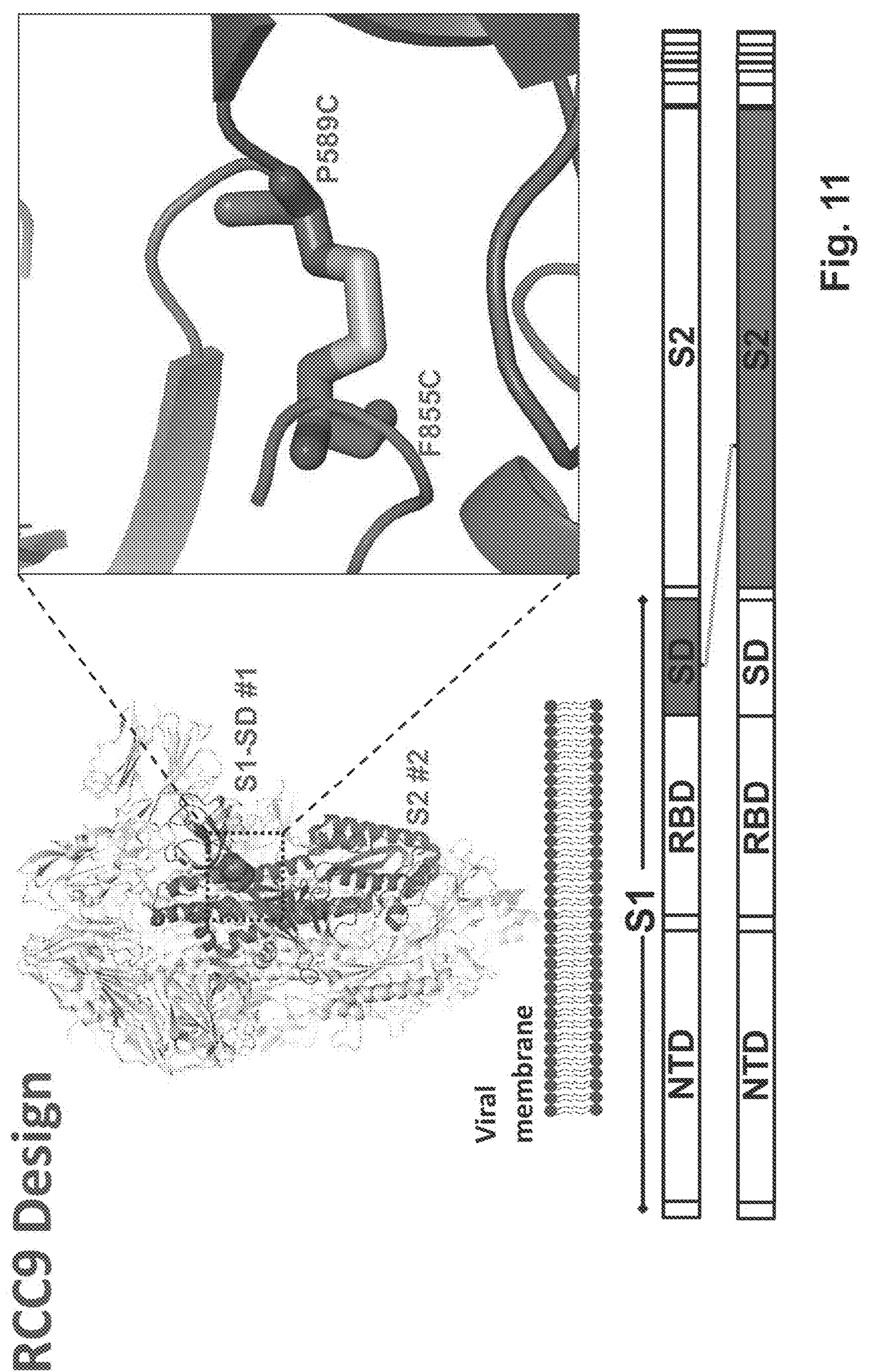
FIG. 11 depicts the positions and structural design of RCC9.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, second ed., Cold Spring Harbor Laboratory Press, Cold Spring Harbor, N.Y. (1989) and Ausubel et al, Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

The term "polypeptide" encompasses native or artificial proteins, protein fragments and polypeptide analogs of a protein sequence. A polypeptide may be monomeric or polymeric.

The term "isolated protein", "isolated polypeptide" or "isolated antibody" is a protein, polypeptide or antibody that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally-associated components by isolation, using protein purification techniques well known in the art.

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide fragment" as used herein refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "immunogen" means a molecule, often a polypeptide, which, when presented to the immune system of a healthy animal to which the molecule is foreign, will elicit some form of immune response against the molecule or a cell, or other organism, displaying the molecule.

The term "antigen" means an immunogen in which, at least part of, the immune response consists of the production of antibodies against the immunogen.

Examples of isolated antibodies include an anti-SARS-CoV2 S protein antibody that has been affinity purified using SARS-CoV2 S protein or a portion thereof, an anti-SARS-CoV2 S protein antibody that has been synthesized by a hybridoma or other cell line in vitro, and a human anti-SARS-CoV2 S protein antibody derived from a transgenic mouse.

In certain embodiments, amino acid substitutions to an anti-SARS-CoV2 S polypeptide are those which: (1) reduce susceptibility to proteolysis, (2) reduce susceptibility to oxidation, (3) alter binding affinity for forming protein complexes, and (4) confer or modify other physicochemical or functional properties of such analogs, but still retain its conformation and ability to act as an immunogen. Analogs can include various muteins of a sequence other than the normally-occurring peptide sequence. For example, single or multiple amino acid substitutions, preferably conservative amino acid substitutions, may be made in the normally-occurring sequence, preferably in the portion of the polypeptide outside the domain(s) forming intermolecular contacts. A conservative amino acid substitution should not substantially change the structural characteristics of the parent sequence; e.g., a replacement amino acid should not alter the anti-parallel β-sheet that makes up the immunoglobulin binding domain that occurs in the parent sequence, or disrupt other types of secondary structure that characterizes the parent sequence. In general, glycine and proline would not be used in an anti-parallel β-sheet. Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et ai, Nature 354:105 (1991), incorporated herein by reference.

Where an "antibody" is referred to herein with respect to the invention, it is normally understood that an antigen-binding portion thereof may also be used. An antigen-binding portion competes with the intact antibody for specific binding. See generally, Fundamental Immunology, Ch. 7 (Paul, W., ed., second ed. Raven Press, N.Y. (1989)) (incorporated by reference in its entirety for all purposes). Antigen-binding portions may be produced by recombinant DNA techniques or by enzymatic or chemical cleavage of intact antibodies. In some embodiments, antigen-binding portions include Fab, Fab', $F(ab')_2$, Fd, Fv, and complementarity determining region (CDR) fragments. Single-chain antibodies (scFv), chimeric antibodies, diabodies and polypeptides that contain at least a portion of an antibody that is sufficient to confer specific antigen binding to the polypeptide can also be prepared.

From N-terminus to C-terminus, both the mature light and heavy chain variable domains comprise the regions FR1, CDR1, FR2, CDR2, FR3, CDR3 and FR4. The assignment of amino acids to each domain herein is in accordance with the definitions of Kabat, Sequences of Proteins of Immunological Interest (National Institutes of Health, Bethesda, Md. (1987 and 1991)), Chothia & Lesk, J Mol Biol. 196:901-917 (1987) or Chothia et al, Nature 342:878-883 (1989).

As used herein, a Fd fragment means an antibody fragment that consists of the VH and CH 1 domains; an Fv fragment consists of the VL and VH domains of a single arm of an antibody; and a dAb fragment (Ward et al, Nature 341:544-546 (1989)) consists of a VH domain.

The term "polynucleotide" as referred to herein means a polymeric form of nucleotides of at least 10 bases in length, either ribonucleotides or deoxynucleotides or a modified form of either type of nucleotide. The term includes single and double stranded forms.

The term "isolated polynucleotide" as used herein means a polynucleotide of genomic, cDNA, or synthetic origin or some combination thereof, which by virtue of its origin the "isolated polynucleotide" (1) is not associated with all or a portion of a polynucleotides with which the "isolated polynucleotide" is found in nature, (2) is operably linked to a polynucleotide to which it is not linked in nature, or (3) does not occur in nature as part of a larger sequence.

The term "naturally occurring nucleotides" as used herein includes deoxyribonucleotides and ribonucleotides. The term "modified nucleotides" as used herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al., Nucl. Acids Res. 14:9081 (1986); Stec et al, J. Am. Chem. Soc. 106:6077 (1984); Stein et al., Nucl. Acids Res. 16:3209 (1988); Zon et al., Anti-Cancer Drug Design 6:539 (1991); Zon et al., Oligonucleotides and Analogues: A Practical Approach, pp. 87-108 (F. Eckstein, Ed., Oxford University Press, Oxford England (1991)); U.S. Pat. No. 5,151,510; Uhlmann and Peyman, Chemical Reviews 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest. The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. One example of "high stringency" or "highly stringent" conditions is the incubation of a polynucleotide with another polynucleotide, wherein one polynucleotide may be affixed to a solid surface such as a membrane, in a hybridization buffer of 6×SSPE or SSC, 50% formamide, 5×Denhardt's reagent, 0.5% SDS, 100 μg/ml denatured, fragmented salmon sperm DNA at a hybridization temperature of 420 C for 12-16 hours, followed by twice washing at 55° C. using a wash buffer of IX SSC, 0.5% SDS. See also Sambrook et ai, supra, pp. 9.50-9.55.

The term "percent sequence identity" in the context of nucleotide sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wisconsin. FASTA, which includes, e.g., the programs FASTA2 and FASTA3, provides alignments and percent sequence identity of the regions of the best overlap between the query and search sequences (Pearson, Methods Enzymol. 183:63-98 (1990); Pearson, Methods Mol. Biol. 132: 185-219 (2000); Pearson, Methods Enzymol. 266:227-258 (1996); Pearson, J Mol. Biol 276:71-84 (1998); incorporated herein by reference). Unless otherwise specified, default parameters for a particular program or algorithm are used. For instance, percent sequence identity between nucleotide sequences can be determined using FASTA with its default parameters (a word size of 6 and the NOPAM factor for the scoring matrix) or using Gap with its default parameters as provided in GCG Version 6.1, incorporated herein by reference.

A reference to a nucleotide sequence encompasses its complement unless otherwise specified. Thus, a reference to a nucleic acid having a particular sequence should be understood to encompass its complementary strand, with its complementary sequence.

As used herein, the terms "percent sequence identity" and "percent sequence homology" are used interchangeably.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

As applied to polypeptides, the term "substantial identity" means that two peptide sequences, when optimally aligned, such as by the programs GAP or BESTFIT using default gap weights as supplied with the programs, share at least 70%, 75% or 80% sequence identity, preferably at least 90% or 95% sequence identity, and more preferably at least 97%, 98% or 99% sequence identity. In certain embodiments, residue positions that are not identical differ by conservative amino acid substitutions. A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity may be adjusted upwards to correct for the conservative nature of the substitution. Means for making this adjustment are well-known to those of skill in the art. See, e.g., Pearson, Methods Mol. Biol. 243:307-31 (1994). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al, Science 256:1443-45 (1992), incorporated herein by reference. A "moderately conservative" replacement is any change having a nonnegative value in the PAM250 log-likelihood matrix.

Amino acid positions or residues are said to "correspond to" each other when two sequences are optimally aligned. Such residues that correspond to each other are often in the same numbered position, but not always, such as when an N-terminally truncated polypeptide is compared to its wild-type counterpart. Often, residues that correspond to each other will be same amino acid, or conservative amino acids to each other. However, in certain situations, including alignments between variants or isoforms, the residues may be different and not conservative amino acids to each other.

Sequence identity for polypeptides is typically measured using sequence analysis software. Protein analysis software matches sequences using measures of similarity assigned to various substitutions, deletions and other modifications, including conservative amino acid substitutions. For instance, GCG contains programs such as "Gap" and "Bestfit" which can be used with default parameters as specified by the programs to determine sequence homology or sequence identity between closely related polypeptides, such as homologous polypeptides from different species of organisms or between a wild type protein and a mutein thereof. See, e.g., GCG Version 6.1 (University of Wisconsin, WI). Polypeptide sequences also can be compared using FASTA using default or recommended parameters, see GCG Version 6.1. FASTA (e.g., FASTA2 and FASTA3) provides alignments and percent sequence identity of the regions of the best overlap between the query and search sequences (Pearson, Methods Enzymol. 183:63-98 (1990); Pearson, Methods MoI. Biol. 132:185-219 (2000)). Another preferred algorithm when comparing a sequence of the invention to a database containing a large number of sequences from different organisms is the computer program BLAST, especially blastp or tblastn, using default parameters as supplied with the programs. See, e.g., Altschul et al, J. Mol. Biol. 215:403-410 (1990); Altschul et al, Nucleic Acids Res. 25:3389-402 (1997).

Human Anti-SARS-CoV2 S Protein Antibodies and Characterization Thereof

In one embodiment, the invention provides humanized anti-SARS-CoV2 S protein antibodies. In another embodiment, the invention provides human anti-SARS-CoV2 S protein antibodies. In some embodiments, human anti-SARS-CoV2 S protein antibodies are produced by immunizing a non-human transgenic animal, e.g., a rodent, whose genome comprises human immunoglobulin genes so that the transgenic animal produces human antibodies.

Binding Affinity of Anti-SARS-CoV2 S Protein Antibodies to SARS-CoV2 S Protein

In some embodiments of the invention, the anti-SARS-CoV2 S protein antibodies bind to SARS-CoV2 S protein with high affinity.

The binding affinity and dissociation rate of an anti-SARS-CoV2 S protein antibody to SARS-CoV2 S protein can be determined by methods known in the art. The binding affinity can be measured by ELISAs, RIAs, flow cytometry, surface plasmon resonance, such as BIACORE™. The dissociate rate can be measured by surface plasmon resonance. Preferably, the binding affinity and dissociation rate is measured by surface plasmon resonance. More preferably, the binding affinity and dissociation rate are measured using BIACORE™. One can determine whether an antibody has substantially the same KD as an anti-SARS-CoV2 S protein antibody by using methods known in the art. Example V exemplifies a method for determining affinity constants of anti-SARS-CoV2 S protein monoclonal antibodies.

Identification of SARS-CoV2 S Protein Epitopes Recognized by Anti-SARS-CoV2 S Protein Antibodies In another embodiment, the invention provides an anti-SARS-CoV2 S protein antibody that inhibits, blocks, or decreases SARS-CoV2 S protein binding to a receptor, in particular, to angiotensin-converting enzyme 2 (ACE2). In another embodiment, the invention provides an anti-SARS-CoV2 S protein antibody that inhibits, blocks, or decreases SARS-CoV2 S protein-mediated viral entry into cells. In another embodiment, the invention provides an anti-SARS-CoV2 S protein antibody that inhibits, blocks, or decreases fusion of viral and cell membranes. In another embodiment, the invention provides an anti-SARS-CoV S protein antibody that decreases viral load. In another embodiment, the invention provides an anti-SARS-CoV2 S protein antibody that inhibits, blocks, or decreases in severity for any period of time symptoms or conditions resulting from SARS-CoV2 infection. In certain embodiments, the invention provides an anti-SARS-CoV2 S protein antibody that inhibits, blocks, or decreases in severity for a day, a week, a month, 6 months, a year, or for the remainder of the subjects life symptoms or conditions resulting from SARS-CoV2 infection by 25, 30, 35, 40, 45, 50, 55, 60, 65, 70, 75, 80, 85, 90, 95, or 100%. In certain embodiments, the invention provides an anti-SARS-CoV2 S protein antibody that may perform any combination of the preceding embodiments.

Methods of Producing Antibodies and Antibody Producing Cell Lines

Immunization

In some embodiments, human antibodies are produced by immunizing a non-human, transgenic animal comprising within its genome some or all of human immunoglobulin heavy chain and light chain loci with a SARS-CoV2 S immunogen. In one embodiment, the non-human animal is a XENOMOUSE™ animal. (Abgenix, Inc., Fremont, CA). XENOMOUSE™ mice are engineered mouse strains that comprise large fragments of human immunoglobulin heavy chain and light chain loci and are deficient in mouse antibody production. See, e.g., Green et al, Nature Genetics 7:13-21 (1994) and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504.

In another aspect, the invention provides a method for making anti-SARS-CoV2 S protein antibodies from non-human, non-mouse animals by immunizing non-human transgenic animals that comprise human immunoglobulin loci with a SARS-CoV2 S immunogen. One can produce such animals using the methods described in the above-cited documents. The methods disclosed in these documents can be modified as described in U.S. Pat. No. 5,994,619, which is hereby incorporated by reference. U.S. Pat. No. 5,994,619 describes methods for producing novel cultured inner cell mass (CICM) cells and cell lines, derived from pigs and cows, and transgenic CICM cells into which heterologous DNA has been inserted. CICM transgenic cells can be used to produce cloned transgenic embryos, fetuses, and offspring. The '619 patent also describes methods of producing transgenic animals that are capable of transmitting the heterologous DNA to their progeny. In preferred embodiments of the current invention, the non-human animals are mammals, particularly rats, sheep, pigs, goats, cattle or horses.

XENOMOUSE™ mice produce an adult-like human repertoire of fully human antibodies and generate antigen-specific human antibodies. In some embodiments, the XENOMOUSE™ mice contain approximately 80% of the human antibody V gene repertoire through introduction of megabase sized, germline configuration fragments of the human heavy chain loci and kappa light chain loci in yeast artificial chromosome (YAC). In other embodiments, XENOMOUSE™ mice further contain approximately all of the human lambda light chain locus. See Mendez et ai, Nature Genetics 15:146-156 (1997), Green and Jakobovits, J. Exp. Med. 188:483-495 (1998), and WO 98/24893, the disclosures of which are hereby incorporated by reference.

In some embodiments, the non-human animal comprising human immunoglobulin genes are animals that have a human immunoglobulin "minilocus". In the minilocus approach, an exogenous Ig locus is mimicked through the inclusion of individual genes from the Ig locus. Thus, one or more VH genes, one or more DH genes, one or more JH genes, a mu constant domain, and a second constant domain (preferably a gamma constant domain) are formed into a construct for insertion into an animal. This approach is described, inter alia, in U.S. Pat. Nos. 5,545,807, 5,545,806, 5,569,825, 5,625,126, 5,633,425, 5,661,016, 5,770,429, 5,789,650, 5,814,318, 5,591,669, 5,612,205, 5,721,367, 5,789,215, and 5,643,763, hereby incorporated by reference.

In another aspect, the invention provides a method for making humanized anti-SARS-CoV2 S immunogen antibodies. In some embodiments, non-human animals are immunized with a SARS-CoV2 S immunogen as described below under conditions that permit antibody production. Antibody-producing cells are isolated from the animals, fused with myelomas to produce hybridomas, and nucleic acids encoding the heavy and light chains of an anti-SARS-CoV S protein antibody of interest are isolated. These nucleic acids are subsequently engineered using techniques known to those of skill in the art and as described further below to reduce the amount of non-human sequence, i.e., to humanize the antibody to reduce the immune response in humans.

In certain aspects, the disclosure provides an immunogen comprising a severe acute respiratory syndrome coronavirus 2 spike ("SARS-CoV2 S") polypeptide, wherein the polypeptide comprises one or more pairs of amino acid substitutions that correspond to residues selected from the group consisting of:

a) V382C and R983C of SEQ ID NO: 1;
b) A520C and K41C of SEQ ID NO: 1;
c) S383C and D985C of SEQ ID NO: 1;
d) D614C and T859C of SEQ ID NO: 1;
e) T547C and N978C of SEQ ID NO: 1;
f) A570C and V963C of SEQ ID NO: 1;
g) P665C and L864C of SEQ ID NO: 1;
h) F562C and P225C of SEQ ID NO: 1; and
i) P589C and F855C of SEQ ID NO: 1;

and wherein the polypeptide is 90%, 91%, 92%, 93%, 94%, 95%, 96%, 97%, and 98% identical to SEQ ID NO: 1.

In certain aspects, the disclosure provides an immunogen comprising a severe acute respiratory syndrome coronavirus 2 spike ("SARS-CoV2 S") polypeptide, wherein the polypeptide comprises one or more pairs of amino acid substitutions that correspond to residues selected from the group consisting of:

a) V382C and R983C of SEQ ID NO: 1;
b) A520C and K41C of SEQ ID NO: 1;
c) S383C and D985C of SEQ ID NO: 1;
d) D614C and T859C of SEQ ID NO: 1;
e) T547C and N978C of SEQ ID NO: 1;
f) A570C and V963C of SEQ ID NO: 1;
g) P665C and L864C of SEQ ID NO: 1;
h) F562C and P225C of SEQ ID NO: 1; and
i) P589C and F855C of SEQ ID NO: 1.

In certain embodiments, the immunogen can comprise more than one of the pairs of amino acid substitutions as shown in a)-i), above. In certain embodiments, the polypeptide comprises amino acid substitutions that correspond to residues D614C, T859C, T547C and N978C.

In certain embodiments, the immunogen can comprise substitutions that can abrogate the cleavage of the SARS-CoV2 S polypeptide by furin. Such substitutions include substitutions of residues that correspond to R682, R683, and R685 of SEQ ID NO: 1. In certain embodiments, the polypeptide further comprises one or more groups of amino acid substitutions that correspond to residues selected from the group consisting of:

a) K986P and V987P of SEQ ID NO: 1;
b) R682G, R683S, and R685S of SEQ ID NO: 1;
c) R682S, R683G, and R685G of SEQ ID NO: 1;
d) R682G, R683S, R685S, K986P and V987P of SEQ ID NO: 1; and
e) R682S, R683G, R685G, K986P and V987P of SEQ ID NO: 1.

In certain embodiments, the polypeptide has at least 97% sequence identity to SEQ ID NO: 1.

In certain embodiments, the polypeptide has at least 98% sequence identity to SEQ ID NO: 1.

In certain embodiments, the polypeptide has at least 99% sequence identity to SEQ ID NO: 1.

In certain embodiments, the polypeptide comprises an amino acid sequence selected from the group consisting of SEQ ID NOs: 13-21.

In certain embodiments, the polypeptide comprises an amino acid sequence selected from the group consisting of SEQ ID NOs: 4-12 and 44-61.

In certain embodiments, the polypeptide comprises a trimerization domain attached to the C-terminus of the immunogen.

In certain embodiments, the trimerization domain comprises the amino acid sequence of SEQ ID NO: 84 or SEQ ID NO: 85.

In certain embodiments, the polypeptide comprises an amino acid sequence selected from the group consisting of SEQ ID NOs: 23-40 and 63-80.

In certain aspects, the disclosure provides a method of producing antibodies that specifically bind SARS-CoV2 S polypeptide comprising administering to a non-human subject an immunogen of the present invention and a pharmaceutically acceptable delivery vehicle and/or adjuvant.

In certain aspects, the disclosure provides a method of treating COVID-19 in a subject comprising administering a therapeutically effective amount of an antibody produced by a method of the present invention and a pharmaceutically acceptable delivery vehicle to the subject.

In certain aspects, the disclosure provides a composition capable of producing an immunological response in a human subject, the composition comprising an immunogen of the present invention and a pharmaceutically acceptable delivery vehicle and/or adjuvant.

Immunization of animals can be by any method known in the art. See, e.g., Harlow and Lane, Antibodies: A Laboratory Manual, New York: Cold Spring Harbor Press, 1990. Methods for immunizing non-human animals such as mice, rats, sheep, goats, pigs, cattle and horses are well known in the art. See, e.g., Harlow and Lane, supra, and U.S. Pat. No. 5,994,619. In one embodiment, the SARS-CoV2 S immunogen is administered with an adjuvant to stimulate the immune response. Exemplary adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with a SARS-CoV2 S immunogen, antibodies and/or antibody-producing cells can be obtained from the animal. In some embodiments, anti-SARS-CoV2 S protein antibody-containing serum is obtained from the animal by bleeding or sacrificing the animal. The serum may be used as it is obtained from the animal, an immunoglobulin fraction may be obtained from the serum, or the anti-SARS-CoV S protein antibodies may be purified from the serum.

In some embodiments, antibody-producing immortalized cell lines are prepared from cells isolated from the immunized animal. After immunization, the animal is sacrificed and lymph node and/or splenic B cells are immortalized by any means known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Immortalized cells are screened using SARS-CoV2 S protein, a portion thereof, or a cell expressing SARS-CoV2 S protein. In one embodiment, the initial screening is performed using an enzyme-linked immunoassay (ELISA) or a radioimmunoassay. An example of ELISA screening is provided in WO 00/37504, incorporated herein by reference.

Anti-SARS-CoV2 S protein antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

In one embodiment, the immunized animal is a non-human animal that expresses human immunoglobulin genes and the splenic B cells are fused to a myeloma cell line from the same species as the non-human animal. In a more preferred embodiment, the immunized animal is a XENOMOUSE™ mouse and the myeloma cell line is a non-secretory mouse myeloma. In an even more preferred embodiment, the myeloma cell line is P3-X63-Ag8.653 (American Type Culture Collection. See, e.g., Example I. [0124J Thus, in one embodiment, the invention provides methods for producing a cell line that produces a human monoclonal antibody or a fragment thereof directed to SARS-CoV2 S protein comprising (a) immunizing a non-human transgenic animal described herein with SARS-CoV2 S immunogen; (b) allowing the transgenic animal to mount an immune response to SARS-CoV2 S immunogen; (c) isolating antibody-producing cells from the transgenic animal; (d) immortalizing the antibody-producing cells; (e) creating individual monoclonal populations of the immortalized antibody-producing cells; and (f) screening the immortalized antibody-producing cells to identify an antibody directed to SARS-CoV2 S.

In another aspect, the invention provides hybridomas that produce a human anti-SARS-CoV2 S protein antibody. In one embodiment, the human anti-SARS-CoV2 S protein antibody produced by the hybridoma is an antagonist of SARS-CoV2 S protein. In some embodiments, the anti-SARS-CoV2 S protein monoclonal antibody does not mediate antibody dependent enhancement of viral infection. In one embodiment, the hybridomas are mouse hybridomas, as described above. In other embodiments, the hybridomas are produced in a non-human, non-mouse species such as rats, sheep, pigs, goats, cattle or horses. In another embodiment, the hybridomas are human hybridomas.

In one embodiment of the invention, antibody-producing cells are isolated and expressed in a host cell, for example myeloma cells. In still another embodiment, a transgenic animal is immunized with a SARS-CoV2 S protein immunogen as described herein, primary cells, e.g., spleen or peripheral blood cells, are isolated from an immunized transgenic animal and individual cells producing antibodies specific for the desired antigen are identified. Polyadenylated mRNA from each individual cell is isolated and reverse transcription polymerase chain reaction (RT-PCR) is performed using sense primers that anneal to variable region sequences, e.g., degenerate primers that recognize most or all of the FR1 regions of human heavy and light chain variable region genes and anti-sense primers that anneal to constant or joining region sequences. cDNAs of the heavy and light chain variable domains are then cloned and expressed in any suitable host cell, e.g., a myeloma cell, as chimeric antibodies with respective immunoglobulin constant regions, such as the heavy chain and K or A constant domains. See Babcook, J. S. et al. (1996) Proc. Natl. Acad. ScL USA 93:7843-48, incorporated herein by reference. Anti SARS-CoV2 S protein antibodies may then be identified and isolated as described herein.

In certain embodiments, a pharmaceutical composition comprising SARS-CoV2 S immunogens is used to elicit an immune response to the SARS-CoV2 S in a vaccine host. Pharmaceutical compositions containing SARS-CoV2 S immunogens of the present invention can be used as a vaccine for prevention and treatment of COVID-19.

Additionally, compositions can contain carriers and/or other additives in a pharmaceutically acceptable delivery system. Accordingly, a composition containing the SARS-CoV2 S immunogens can be formulated as a pharmaceutical vaccine formulation using adjuvants, pharmaceutically-acceptable carriers or other ingredients including immunological adjuvants routinely provided in vaccine formulations. An immunologic adjuvant is defined as "any substance that acts to accelerate, prolong, or enhance antigen-specific immune responses without having any specific antigenic effect in itself when used in combination with specific vaccine antigens." There are many known adjuvants in widespread use, including oils, aluminum salts, and virosomes. Two common salts including aluminum phosphate (e.g. Adjuphos) and aluminum hydroxide (e.g. Alhydrogel) are the most common adjuvants in human vaccines. Methods for selecting mineral salts and determining the preferred concentration of mineral salt to employ or combinations thereof are well known to those skilled in the art.

Among other ingredients that can also be used as adjuvants in this invention include liposyn, saponin, squalene, L121, Emulsigen, monophosphoryl lipid A (MPL), QS21, ISA35, ISA206, ISA50V, ISA51, and ISA720 as well as the other efficacious adjuvants and emulsifiers. In a particular embodiment, the delivery vehicle and adjuvant is Montanide™ ISA51 (an oil vaccine adjuvant composition comprised of vegetable oil and mannide oleate for production of water-in-oil emulsions), Tween® 80 (also known as: Polysorbate 80 or Polyoxyethylene (20) sorbitan monooleate), a CpG oligonucleotide, and/or any combination thereof. In another embodiment, the pharmaceutical composition is a water-in-oil-in-water (i.e. w/o/w) emulsion with Emulsigen or Emulsigen D as the adjuvant.

Pharmaceutical compositions as vaccines can be formulated as immediate-release or sustained-release formulations. Additionally, the pharmaceutical compositions can be formulated for induction of systemic or localized mucosal, immunity through immunogen entrapment and co-administration with microparticles. Such delivery systems are readily determined by one of ordinary skill in the art.

Various vaccine formulations containing SARS-CoV2 S immunogens of the present disclosure are effective for protecting and treatment of SARS-CoV2 infection and COVID-19.

The present invention also encompasses nucleic acid molecules encoding SARS-CoV2 S immunogens. In one embodiment, the nucleic acid encodes a SARS-CoV2 immunogen of the invention.

The invention provides vectors comprising nucleic acid molecules that encode the SARS-CoV2 immunogen of the invention.

In some embodiments, the SARS-CoV2 immunogen of the invention are expressed by inserting DNAs encoding SARS-CoV2 immunogen into expression vectors such that the DNA is operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The DNA is ligated into a vector such that transcriptional and translational control sequences within the vector serve their intended function of regulating the transcription and translation of the SARS-CoV2 immunogen. The expression vector and expression control sequences are chosen to be compatible with the expression host cell used. The DNA is inserted into the expression vector by standard methods (e.g., ligation of complementary restriction sites on the antibody gene fragment and vector, or blunt end ligation if no restriction sites are present).

A convenient vector is one that encodes a functionally complete SARS-CoV2 immunogen DNA sequence, with appropriate restriction sites engineered. Polyadenylation and transcription termination occur at native chromosomal sites downstream of the coding regions. The recombinant expression vector also can encode a signal peptide that facilitates secretion of the SARS-CoV2 immunogen from a host cell. The DNA may be cloned into the vector such that the signal peptide is linked in-frame to the amino terminus of the SARS-CoV2 immunogen. The signal peptide can be an immunoglobulin signal peptide or a heterologous signal peptide (i.e., a signal peptide from a non-immunoglobulin protein). In certain embodiments, a signal peptide having the amino acid sequence of MFVFLVLLPLVSSQCV (SEQ ID NO: 86) is fused to the amino terminus of any of the polypeptide sequences of the present invention. In certain embodiments, a signal peptide having the amino acid sequence of MDMRVPAQLLGLLLLWLRGARC (SEQ ID NO: 87) is fused to the amino terminus of any of the polypeptide sequences of the present invention. In other embodiments, a signal peptide having the amino acid sequence of MAWALLLLTLLTQGTGSWA (SEQ ID NO: 88) is fused to the amino terminus of any of the polypeptide sequences of the present invention. In still other embodiments, a signal peptide having the amino acid sequence of MTCSPLLLTLLIHCTGSWA (SEQ ID NO: 89) is fused to the amino terminus of any of the polypeptide sequences of the present invention. Other suitable signal peptide sequences that can be fused to the amino terminus of the polypeptide sequences described herein include: MEAPAQLLFLLLLWLPDTTG (SEQ ID NO: 90), MEWTWRVLFLVAAATGAHS (SEQ ID NO: 91), METPAQLLFLLLLWLPDTTG (SEQ ID NO: 92), METPAQLLFLLLLWLPDTTG (SEQ ID NO: 93), MKHLWFFLLLVAAPRWVLS (SEQ ID NO: 94), and MEWSWVFLFFLSVTTGVHS (SEQ ID NO: 95), and MGILPSPGMPALLSLVSLLSVLLMGCVAETGTQC (SEQ ID NO: 96). Other signal peptides are known to those of skill in the art and may be fused to any of the polypeptide chains of the present invention, for example, to facilitate or optimize expression in particular host cells.

In addition to the antibody chain genes, the recombinant expression vectors of the invention carry regulatory sequences that control the expression of the SARS-CoV2 immunogen in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods for expressing antibodies in plants, including a description of promoters and vectors, as well as transformation of plants is known in the art. See, e.g., U.S. Pat. No. 6,517,529, incorporated herein by reference. Methods of expressing polypeptides in bacterial cells or fungal cells, e.g., yeast cells, are also well known in the art.

In addition to the SARS-CoV2 immunogen DNA and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, incorporated herein by reference). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification), the neo gene (for G418 selection), and the glutamate synthetase gene.

Nucleic acid molecules encoding SARS-CoV2 immunogenz and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide (s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455, incorporated herein by reference). Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, N50 cells, SP2 cells, HEK-293T cells, NIH- 3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 or Sf21 cells. When recombinant expression vectors encoding SARS-CoV2 immunogens are introduced into mammalian host cells, the immunogens are produced by culturing the host cells for a period of time sufficient to allow for expression of the immunogen in the host cells or, more preferably, secretion of the SARS-CoV2 immunogen into the culture medium in which the host cells are grown. SARS-CoV2 immunogens can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris.*

Further, expression of SARS-CoV2 immunogens of the invention from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, 0 323 997 and 0 338 841.

In another aspect, the invention provides diagnostic methods. The SARS-CoV2 immunogen can be used to detect SARS-CoV2 S antibodies in a biological sample in vitro or in vivo. In one embodiment, the invention provides a method for diagnosing the presence or location of SARS-CoV2 antibodies in a subject in need thereof.

The SARS-CoV2 immunogen can be used in a conventional immunoassay, including, without limitation, an ELISA, an RIA, flow cytometry, tissue immunohistochemistry, Western blot or immunoprecipitation. The SARS-CoV2 immunogen of the invention can be used to detect SARS-CoV2 S antibodies from humans.

The invention provides a method for detecting SARS-CoV2 S antibody in a biological sample comprising contacting the biological sample with an SARS-CoV2 immunogen of the invention and detecting the bound antibody. In one embodiment, the SARS-CoV2 immunogen is directly labeled with a detectable label. In another embodiment, the SARS-CoV2 immunogen is unlabeled and a second antibody or other molecule that can bind the SARS-CoV2 immunogen is labeled.

Suitable labels include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include 1251, 1311, 35S or 3H.

In another embodiment, the invention provides a method for neutralizing SARS-CoV by administering an anti-SARS-CoV2 S protein antibody produced using a SARS-CoV2 immunogen of the invention to a patient in need thereof. Any of the types of antibodies described herein may be used therapeutically. In various embodiments, the anti-SARS-CoV S protein antibody is a human antibody.

In some embodiments, the patient is a human patient. Alternatively, the patient may be a mammal infected with SARS-CoV2. The antibody may be administered to a non-human mammal infected with SARS for veterinary purposes or as an animal model of human disease. Such animal models may be useful for evaluating the therapeutic efficacy of antibodies of this invention.

In one embodiment, the invention provides methods of treating, aiding in the treatment, preventing or aiding in the prevention of, SARS-CoV2 infection and conditions or disorders resulting from such infection, in a subject by administering to the subject a therapeutically-effective amount of an anti-SARS-CoV2 S protein antibody of the invention.

The antibody may be administered once, but more preferably is administered multiple times. The antibody may be administered from three times daily to once every six months or longer. The administering may be on a schedule such as three times daily, twice daily, once daily, once every two days, once every three days, once weekly, once every two weeks, once every month, once every two months, once every three months and once every six months. The antibody may also be administered continuously via a minipump. The antibody may be administered via an oral, mucosal, buccal, intranasal, inhalable, intravenous, subcutaneous, intramuscular, parenteral, intratumor or topical route. The antibody may be administered locally or systemically.

The therapeutic compositions comprising anti-S ARS-CoV S protein antibodies may be administered to the subject, for example, orally, nasally, vaginally, buccally, rectally, via the eye, or via the pulmonary route, in a variety of pharmaceutically acceptable dosing forms, which will be familiar to those skilled in the art.

For example, the anti-SARS-CoV S protein antibodies may be administered via the nasal route using a nasal insufflator device. Examples of these are already employed for commercial powder systems intended for nasal application (e.g. Fisons Lomudal System). Details of other devices can be found in the pharmaceutical literature (see for example Bell, A. Intranasal Delivery devices, in Drug Delivery Devices Fundamentals and Applications, Tyle P. (ed), Dekker, New York, 1988).

The anti-SARS-CoV2 S protein antibodies can be administered to the vagina in a freeze dried powder formulation. Anti-SARS-CoV2 S protein antibodies may be administered in a vaginal applicator and once in the vagina, the formulation comprising the anti-SARS-CoV2 S protein antibodies are released by pressing a syringe-type piston or similar release mechanism on the applicator. Alternatively, the anti-SARS-CoV2 S protein antibodies may be formulated as a powder using a powder device, formulated into a vagina suppository or pessary or vaginal tablet or vaginal gel.

The anti-SARS-CoV2 S protein antibodies can also be administered to the eye in a gel formulation. For example, before administration, a formulation containing the anti-SARS-CoV2 S protein antibodies may be conveniently contained in a two compartment unit dose container, one compartment containing a freeze-dried anti-SARS-CoV2 S protein antibody preparation and the other compartment containing normal saline. Prior to application, the two compartments are mixed and a gel is formed, which is then administered to the eye.

Other delivery routes for the anti-SARS-CoV2 S protein antibodies include via the pulmonary route using a powder inhaler or metered dose inhaler, via the buccal route formulated into a tablet or a buccal patch, via the rectal route formulated into suppositories; and via the oral route in the form of a tablet, a capsule or a pellet (which compositions may administer agent via the stomach, the small intestine or the colon), all of which may be formulated in accordance with techniques which are well known to those skilled in the art.

The antibody may be administered once, at least twice or for at least the period of time until the condition is treated, palliated or cured. The antibody will generally be administered as part of a composition as described supra. The dosage of antibody will generally be in the range of 0.1-100 mg/kg, more preferably 0.5-50 mg/kg, more preferably 1-20 mg/kg, and even more preferably 1-10 mg/kg. The serum concentration of the antibody may be measured by any method known in the art.

In another embodiment, the antibodies of the present invention are administered to the subject in combination with other therapeutic agents. In one embodiment, the additional therapeutic agents may be treat the symptoms of the SARS-CoV2 infection on their own, and may optionally synergize with the effects of the antibodies. The additional agent that is administered may be selected by one skilled in the art for treating the infection.

Co-administration of the antibody with an additional therapeutic agent (combination therapy) encompasses administering a composition comprising the anti-SARS-CoV2 S protein antibody and the additional therapeutic agent as well as administering two or more separate compositions, one comprising the anti-SARS-CoV2 S protein antibody and the other(s) comprising the additional therapeutic agent(s). Further, although coadministration or combination therapy generally means that the antibody and additional therapeutic agents are administered at the same time as one another, it also encompasses instances in which the antibody and additional therapeutic agents are administered at different times. For instance, the antibody may be administered once every three days, while the additional therapeutic agent is administered once daily. Alternatively, the antibody may be administered prior to or subsequent to treatment with the additional therapeutic agent, for example after a patient has failed therapy with the additional agent. Similarly, administration of the anti-SARS-CoV2 S protein antibody may be administered prior to or subsequent to other therapy.

The antibody and one or more additional therapeutic agents (the combination therapy) may be administered once, twice or at least the period of time until the condition is treated, palliated or cured. Preferably, the combination therapy is administered multiple times. The combination therapy may be administered from three times daily to once every six months. The administering may be on a schedule such as three times daily, twice daily, once daily, once every two days, once every three days, once weekly, once every two weeks, once every month, once every two months, once every three months and once every six months, or may be administered continuously via a minipump. The combination therapy may be administered via an oral, mucosal, buccal, intranasal, inhalable, intravenous, subcutaneous, intramuscular, or parenteral.

In certain aspects, the disclosure provides a method for treating, preventing or alleviating the symptoms of a SARS-CoV2-mediated disorder in a subject in need thereof, comprising the step of administering to the subject an antibody or antigen-binding portion according to any one of the preceding embodiments.

In certain embodiments, antibodies with different binding specificities may be used in combination to simultaneously target several neutralizing epitopes and prevent emergence of escape mutants. In certain embodiments, neutralizing epitopes may include regions of S1 or S2, other SARS-CoV2 proteins, or S protein receptors. In certain embodiments, the neutralizing epitopes are in the S1 RBD domain or upstream of the RBD.

In certain embodiments, antibodies with binding specificities to a plurality of viral strains may be used in combination to simultaneously target multiple viral strains. In certain embodiments, an antibody may find to a single strain or multiple strains. A number of SARS-CoV2 strains have been described and are known to one of skill in the art.

In order that this invention may be better understood, the following examples are set forth. These examples are for purposes of illustration only and are not to be construed as limiting the scope of the invention in any manner.

Example 1

Proline mutations in the coiled-coiled regions of coronavirus S proteins and other viruses have been shown to improve expression levels and stability. However, cryo-EM studies demonstrate that roughly 50% of all molecules still maintain one RBD in the "up" conformation, suggesting these methods are only partially successful at stabilizing the S protein in the prefusion state (FIG. 1). A structure-based, rational design was used to design covalent disulfides between different domains of the S-protein. Nine double-cysteine mutations were identified that have the potential to form inter-domain and inter-protomer disulfides with the express goal of limiting the capability of the RBD to transition to the "up" conformation.

These mutations were identified by scanning a recent cryo-EM structure of the closed CoV-2 S ectodomain (pdb: 6VXX). Briefly, all residue pairs existing either inter-domain or inter-protomer with a Cβ of <6.5 Å were computationally modeled as a disulfide pair and scored for energetic potential, emphasizing variants which minimized perturbations to the original structure. Variants were filtered by score, and nine were selected for further evaluation (FIG. 2). These 9 disulfide variants could be classified into 3 broad clusters: linking the RBD to the NTD, linking the RBD to the S2, and linking the SD1/SD2 to the S2.

These efforts represent a strategy for further development into prefusion stabilized viral proteins. Although the disulfides described here are specific to SARS-CoV-2 S proteins, this method can be adapted to other coronaviruses and proteins (viral or otherwise) where a preferred conformation is desired.

Example 2

Immunization and Hybridoma Production

Five micrograms of purified S protein is emulsified in Titermax Gold adjuvant (Sigma) and 6-10 week old IgG2K XenoMouse animals are immunized intraperitoneally. Subsequent boosts are performed sequentially using TiterMax Gold or alum (Sigma) as adjuvants. When the animals developed an anti-S antibody response, a final boost in PBS is performed, four days later the spleen and lymph cells re harvested, fused with P3 myeloma cells and HPRT+ hybridomas are selected in hypoxanthine-azaserine (HA) using a standard protocol (Davis).

Hybridoma supernatants are individually screened for S reactivity by ELISA against S-V5-HIS with a counter screen against OVA-V5-HIS as a control. Hybridoma supernatants yielding OD values above 0.7 when tested against S-V5-HIS (Tor2) are further tested against various S1-Ig fragments by ELISA.

SEQUENCE LISTING

The patent contains a lengthy sequence listing. A copy of the sequence listing is available in electronic form from the USPTO web site (https://seqdata.uspto.gov/docdetail?docId=US12709636B2). An electronic copy of the sequence listing will also be available from the USPTO upon request and payment of the fee set forth in 37 CFR 1.19(b)(3).

We claim:

1. An immunogen comprising a severe acute respiratory syndrome coronavirus 2 spike ("SARS-CoV2 S") polypeptide, wherein the polypeptide comprises any one of SEQ ID NOs: 13-21.

2. The immunogen of claim 1, wherein the polypeptide comprises a trimerization domain attached to the C-terminus of the polypeptide.

3. The immunogen of claim 2, wherein the trimerization domain comprises the amino acid sequence of SEQ ID NO: 84 or SEQ ID NO: 85.

4. The immunogen of claim 3, wherein the polypeptide comprises an amino acid sequence selected from the group consisting of SEQ ID NOs: 32-40.

5. A method of producing antibodies that specifically bind SARS-CoV2 S polypeptide comprising administering to a non-human subject the immunogen of any one of claims 1 and 2-4 and a pharmaceutically acceptable delivery vehicle and/or adjuvant.

6. A method of treating COVID-19 in a subject comprising administering a therapeutically effective amount of an antibody produced by the method of claim 5 and a pharmaceutically acceptable delivery vehicle to the subject.

7. A composition capable of producing an immunological response in a human subject, the composition comprising the immunogen of any one of claims 1 and 2-4 and a pharmaceutically acceptable delivery vehicle and/or adjuvant.

* * * * *